United States Patent
Dupelle et al.

(10) Patent No.: US 6,782,293 B2
(45) Date of Patent: Aug. 24, 2004

(54) DEFIBRILLATION ELECTRODE ASSEMBLY INCLUDING CPR PAD

(75) Inventors: Michael R. Dupelle, Attleboro, MA (US); Deborah T. Jones, Dartmouth, MA (US); Ward Hamilton, Amherst, NH (US); Frederick W. Faller, Burlington, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 09/952,837

(22) Filed: Sep. 14, 2001

(65) Prior Publication Data

US 2003/0055477 A1 Mar. 20, 2003

(51) Int. Cl.[7] .................................................. A61N 1/04
(52) U.S. Cl. ........................... 607/142; 607/5; 607/152
(58) Field of Search ...................... 601/41, 44; 600/372, 600/386, 388–390, 393; 607/4–5, 115, 142, 148–150, 152–153

(56) References Cited

U.S. PATENT DOCUMENTS

| | | |
|---|---|---|
| 521,594 A | 6/1894 | Miles |
| 631,733 A | 8/1899 | Bonfils et al. |
| 4,121,575 A * | 10/1978 | Mills et al. .................. 600/382 |
| 4,355,634 A * | 10/1982 | Kanter ......................... 601/41 |
| 4,809,683 A * | 3/1989 | Hanson ........................ 601/41 |
| 5,010,896 A | 4/1991 | Westbrook ................... 128/798 |
| 5,078,134 A | 1/1992 | Heilman et al. ............. 128/421 |
| 5,184,620 A | 2/1993 | Cudahy et al. .............. 128/639 |
| 5,356,428 A * | 10/1994 | Way ............................ 607/142 |
| 5,443,494 A | 8/1995 | Paolizzi et al. .............. 607/149 |
| 5,466,244 A | 11/1995 | Morgan .......................... 607/5 |
| 5,938,597 A | 8/1999 | Stratbucker ................. 600/382 |
| 5,995,861 A | 11/1999 | Price ........................... 600/372 |
| 6,006,125 A * | 12/1999 | Kelly et al. .................. 600/382 |
| 6,075,369 A * | 6/2000 | Morgan ....................... 324/556 |
| 6,101,413 A * | 8/2000 | Olson et al. ................... 607/5 |
| 6,157,851 A * | 12/2000 | Kelly et al. .................. 600/386 |
| 6,178,357 B1 * | 1/2001 | Gliner et al. ................ 607/142 |
| 6,259,939 B1 * | 7/2001 | Rogel .......................... 600/390 |
| 6,390,996 B1 * | 5/2002 | Halperin et al. .............. 601/41 |
| 6,463,327 B1 * | 10/2002 | Lurie et al. .................... 607/42 |

OTHER PUBLICATIONS

Description of CPR Devices Ltd. CardioPress™ and Moni-Press.

* cited by examiner

Primary Examiner—Kennedy Schaetzle
Assistant Examiner—Kristen Droesch
(74) Attorney, Agent, or Firm—Fish & Richardson P.C.

(57) ABSTRACT

Electrode assemblies are provided, in which a pair of electrodes is joined by a central member. In some implementations, the electrode assemblies are foldable, and are configured to facilitate correct placement on a patient's chest. Some electrode assemblies include a separable electrode, allowing the electrode assembly to be fitted to patients having particularly large chests.

43 Claims, 12 Drawing Sheets

DEFIBRILLATION ELECTRODE ASSEMBLY INCLUDING CPR PAD

TECHNICAL FIELD

This invention relates to medical electrode assemblies, and more particularly to electrode assemblies for use with external defibrillators.

BACKGROUND

Electrodes are used in a wide variety of medical applications. For example, electrodes are used with external defibrillators, to deliver a defibrillating shock to a patient.

Typically, two separate electrodes are applied to the patient for defibrillation treatments. In order for the defibrillating shock to be effective, it is important that the electrodes be positioned so that current flowing from one electrode to the other passes along a straight line that intersects or passes close to the patient's heart (ideally through the ventricles). It is also necessary that good skin contact be made between the electrodes and the patient's skin.

It may be difficult for lay or even skilled caregivers to position the electrodes correctly during emergency treatment. It may also be difficult to get good skin contact, particularly if the electrodes do not conform well to the body contours of the patient. Delay in correct positioning of defibrillator electrodes can mean the difference between life and death to a victim of cardiac arrest.

SUMMARY

The invention features electrode assemblies that can be quickly and accurately positioned on a patient during emergency treatment, and provide good skin contact during use. The electrode assemblies are easy to use, and can be used by most lay caregivers. Moreover, the electrode assemblies of the invention are configured so that a single size electrode assembly can be used to effectively treat patients having a wide variety of chest sizes. In some implementations, the electrode assembly folds for convenient and compact storage.

The electrode assemblies of the invention are easy for lay and skilled caregivers to position quickly and accurately on patients of different sizes and shapes. The variation in the distance between the centerline of the chest and the mid-axillary line on the side of a person's body (a measure of the person's girth) in different individuals can be up to 8 inches or more. In preferred implementations the electrode assembly includes a separable electrode to compensate for these variations.

In one aspect, the invention features an electrode assembly for use with a defibrillator, including a pair of electrodes configured to be attached to a patient's chest, to acquire data indicative of the patient's heart rhythm and to deliver a defibrillating shock if appropriate, and a central member joining the electrodes, the electrodes being folded about the central member.

Some implementations may include one or more of the following features. The electrodes are folded along defined hinge regions. The electrodes are positioned about the central member to facilitate their placement on the chest in an optimal position for the delivery of defibrillation therapy. At least one of the electrodes is joined to the central member by a web of flexible material. The central member includes two portions that are foldable upon each other. The electrodes extend substantially transversely from opposite sides of the central member in a spaced relationship.

The electrode assembly may also include a CPR pad, mounted on the central member. Preferably, the CPR pad is configured to be pressed upon by a caregiver during the delivery of CPR chest compressions, and located on the assembly so that when it is placed on the patient's lower sternum the defibrillation electrodes are properly placed for the delivery of defibrillation therapy. The CPR pad may include a sensor constructed to acquire data indicative of the depth and rate of CPR compressions.

One of the electrodes may be separable from the central member, to accommodate larger patients. The separable electrode may be joined to the central member by a separable flexible fastener, e.g., a separable hinge or hook and loop fastener tape.

The electrode assembly may also include indicia on an exposed surface of the electrode assembly, the indicia including a first portion and a second portion, the indicia being positioned so that alignment of the first portion with a patient's nipples and alignment of the second portion with the patient's sternum will correctly position the electrodes on the patient's chest for effective defibrillation treatment. The indicia may be in the form of cross-hairs, and may be disposed on a CPR pad mounted on the central member or directly on a surface of the central member.

In another aspect, the invention features an electrode assembly for use with a defibrillator, including a pair of electrodes configured to be attached to a patient's chest, to acquire data indicative of the patient's heart rhythm and to deliver a defibrillating shock if appropriate; a central member joining the electrodes; and a CPR pad mounted on the central member, the CPR pad being contoured to receive a caregiver's hand while the caregiver applies chest compressions to the patient.

Some implementations may include one or more of the following features. The CPR pad includes a concave upper surface shaped to facilitate placement of the caregiver's hand. The CPR pad includes a convex lower surface shaped to conform to the patient's sternal notch area. The CPR pad includes a sensor constructed to acquire data indicative of the depth and/or rate of CPR compressions.

In a further aspect, the invention features an electrode assembly for use with a defibrillator, including (a) a pair of electrodes configured to be attached to a patient's chest, to acquire data indicative of the patient's heart rhythm and to deliver a defibrillating shock if appropriate, (b) a central member joining the electrodes, and (c) an indicia on an exposed surface of the electrode assembly, the indicia including a first portion and a second portion, the indicia being positioned so that alignment of the first portion with a patient's nipples and alignment of the second portion with the patient's sternum will correctly position the electrodes on the patient's chest for effective defibrillation treatment.

Some implementations may include one or more of the following features. The indicia may be located so that when the indicia are aligned with the nipples and sternum the indicia will indicate to a caregiver where the caregiver's hands should be placed during the delivery of CPR chest compressions. The indicia may be disposed on the central member, or, alternatively, on a CPR pad, mounted on the central member.

The invention also features an electrode assembly for use with a defibrillator, including (a) an apex electrode and a sternum electrode, the electrodes being configured to be attached to a patient's chest, to acquire data indicative of the patient's heart rhythm and to deliver a defibrillating shock if appropriate; and (b) a central member joining the electrodes;

wherein one of the electrodes is separably joined to the central member.

Some implementations may include one or more of the following features. The separably joined electrode is the apex electrode. The separably joined electrode, after separation from the central member, is joined to the central member only by an electrical connector. The separably joined electrode is joined to the central member by a separable flexible fastener, e.g., a separable hinge or a hook and loop fastener tape. The separable hinge includes a locking pin constructed to be removed by a caregiver to separate the hinge.

In yet another aspect, the invention features an electrode assembly for use with a defibrillator, including (a) an apex electrode and a sternum electrode, the electrodes being configured to be attached to a patient's chest, to acquire data indicative of the patient's heart rhythm and to deliver a defibrillating shock if appropriate, and (b) a central member joining the electrodes, wherein the electrodes extend generally transversely from opposite sides of the central member in a spaced relationship.

Some implementations may include one or more of the following features. The electrodes are positioned about the central member to facilitate their placement on the chest in an optimal position for the delivery of defibrillation therapy. The electrodes are positioned about the central member to minimize contact of the electrodes with breast tissue of the patient. The apex electrode is joined to the central member by a hinge, allowing the apex electrode to be maneuvered around breast tissue. The central member is elongated. The electrodes have a combined active area of at least 150 $cm^2$. Each electrode has an active area of at least 50 $cm^2$, e.g., at least 75 $cm^2$. The electrodes and central member define a "stairstep-like" shape. The central member is dimensioned to fit in the valley between the breasts of the patient. The electrodes extend substantially perpendicular to the central member.

In a further aspect, the invention features an electrode assembly for use with a defibrillator, including (a) a pair of electrodes configured to be attached to a patient's chest, to acquire data indicative of the patient's heart rhythm and to deliver a defibrillating shock if appropriate, (b) a central member joining the electrodes; and (c) a CPR pad positioned on the central member, the electrodes being folded about the central member in a manner so that the CPR pad is on top and can be grasped by a caregiver to unfold the electrode.

Preferably, the electrodes are folded in a manner so that when the CPR pad is grasped by a user the electrodes fall open in the general position in which the electrodes should be applied to the patient.

The invention also features an electrode assembly that includes (a) a pair of electrodes configured to be attached to a patient's chest, to acquire data indicative of the patient's heart rhythm and to deliver a defibrillating shock if appropriate, and (b) a central member joining the electrodes, the electrodes being folded about the central member and the electrode assembly further including labeling indicating how a caregiver should unfold the electrode assembly and apply it to a patient.

The labeling may include a series of graphics configured to illustrate the proper procedure for applying the electrode assembly.

In each of the aspects of the invention discussed above, the electrode assembly may further include lead wires configured to electrically connect the electrodes to the defibrillator, in which case it is preferred that, prior to use, the lead wires are substantially completely enclosed within the electrode assembly. The electrode assemblies may also include a release sheet, mounted on a surface of each electrode to protect the electrodes, the release sheet being configured to be removable when the electrode is positioned adjacent the patient's skin.

Each of the aspects of the invention discussed above may include any desired combination of the features that are described above.

Other features and advantages of the invention will be apparent from the description and drawings, and from the claims.

DETAILED DESCRIPTION

Electrode Assembly Structure

Figure 1:
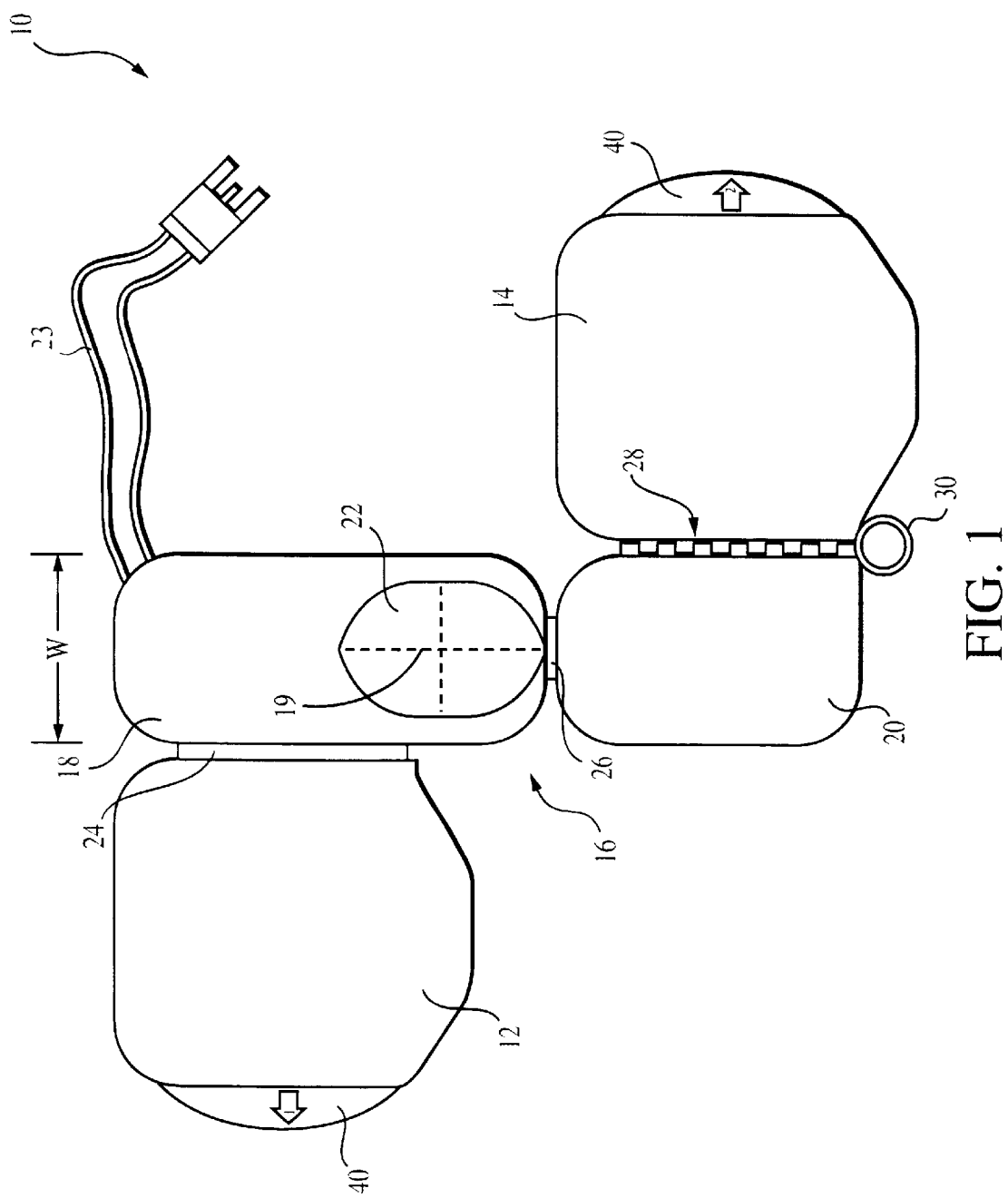
FIG. 1 is a top view of an electrode assembly according to one embodiment of the invention, in its unfolded state.
Figure 3:
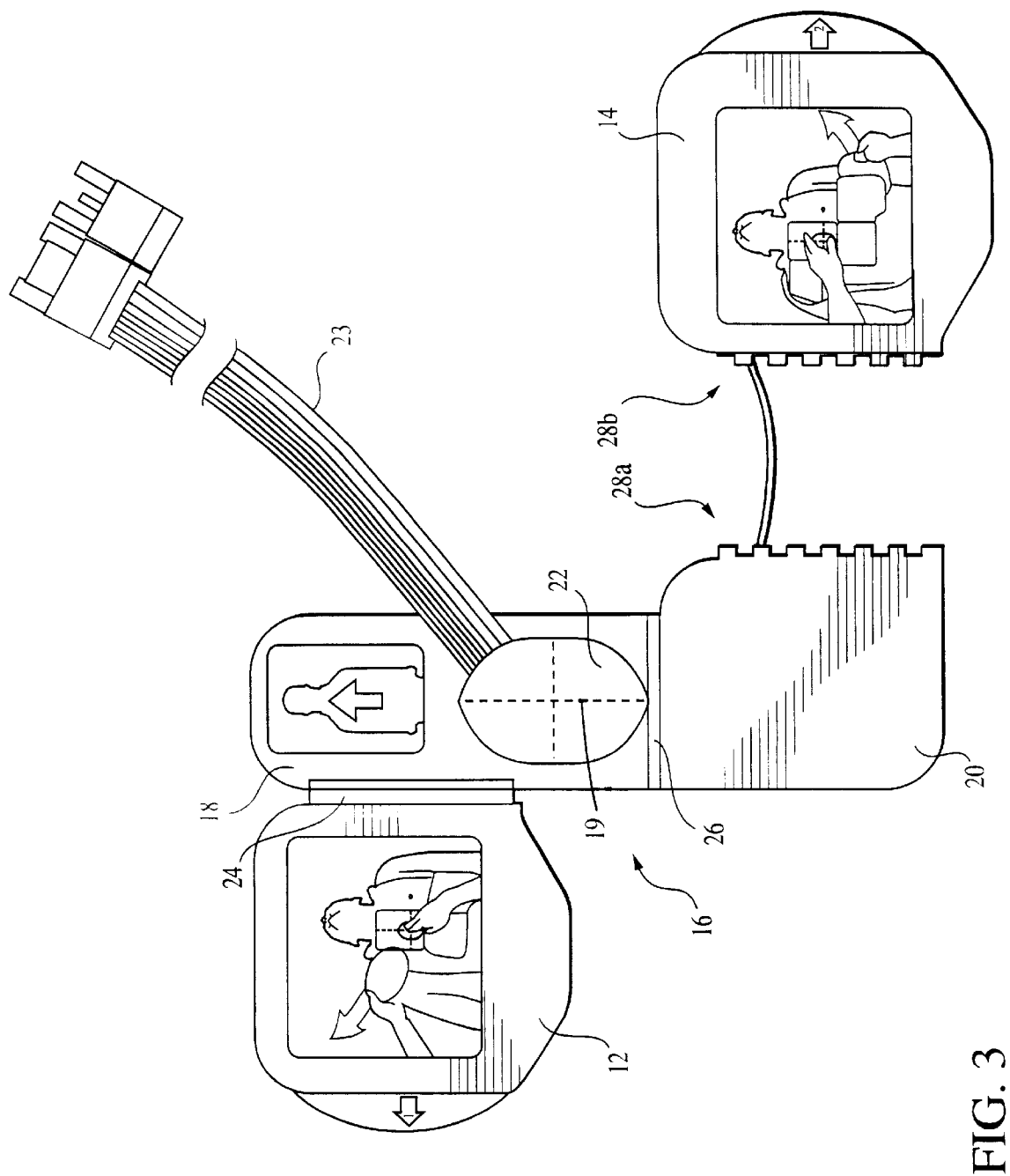
FIG. 3 is a top view of the electrode assembly of FIG. 1, unfolded and with the apex electrode separated and extended.
Figure 3B:
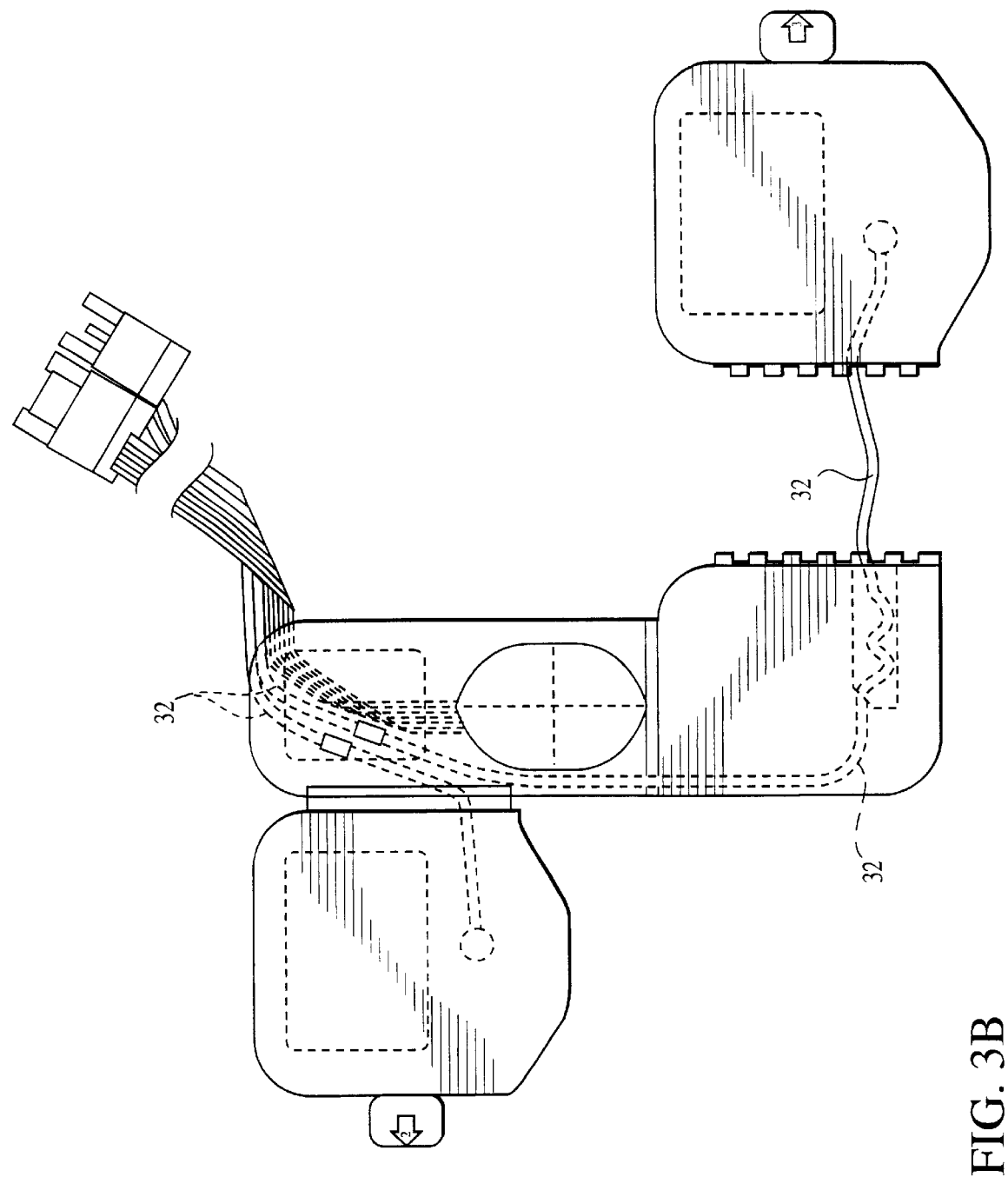
FIG. 3B is similar to FIG. 3, but shows the internal structure of the electrode assembly in dotted lines.

Referring to FIG. 1, an electrode assembly 10, for use with an external defibrillator, includes a sternum electrode 12, an apex electrode 14, and a central member 16 joining the two electrodes. Central member 16 includes an upper central portion 18 and a lower central portion 20. A CPR pad 22, the function of which will be described below, is mounted on upper central portion 18. A cable 23 is provided to connect the electrode assembly to the control box of a defibrillator. Lead wires (for delivery of defibrillation currents and for ECG monitoring)(not shown) run from the cable to the sternum electrode, and from the cable through the central member and to the apex electrode. Wires from the cable may also run through the central member to the CPR pad in order to support the CPR pad's use as a CPR compression-monitoring device. An example of the routing of the lead wires and positioning of the electrodes is shown in FIG. 3B.

The CPR pad 22 has cross-hairs 19 printed or embossed on its top surface, which may be used to correctly position the electrodes. They may, also, be used to help locate the CPR pad on the lower sternum where CPR compressions can be delivered by pressing on the top surface of the CPR pad after electrode attachment. The CPR pad is located on the central member 16 so that when the electrode assembly is correctly positioned on a patient the horizontal cross-hair will be aligned with the patient's nipples and the vertical cross-hair will be aligned with the center line of the patient's sternum.

Each electrode includes a release sheet (not shown) to protect the electrode adhesive and gel. The release sheets include a pull tab 40, and are configured to be removed while the electrode is positioned against a patient's skin. Suitable release sheets that may be removed in this manner are described below in the "Release Sheets" section. Pull tabs 40 include numbers, that, in conjunction with appropriate package instructions and/or electrode labeling (FIG. 7) indicate to the caregiver the proper sequence for applying the electrodes and removing the release sheets from the electrodes, as will be discussed below with reference to FIGS. 4 and 4A.

The sternum electrode 12 is joined to the upper central portion 18 by a flexible web 24. Similarly, the upper central portion 18 is joined to the lower central portion 20 by a flexible web 26. The apex electrode 14 is joined to the lower central portion by a separable hinge 28.

Separable hinge 28 allows the apex electrode to be separated from the lower central portion 20 by pulling locking pin 30 downward. As shown in FIG. 3, removing locking pin 30 causes separable hinge to separate into two halves 28a, 28b. As a result, apex electrode 14 is connected to the lower central portion only by lead wire 32. Extra lead wire is provided (wound up inside of lower central portion 20 prior to separation of the apex electrode) to allow the apex electrode to be extended to accommodate large-chested patients. Typically an extra length of about 10–15 cm is provided.

Figure 8:
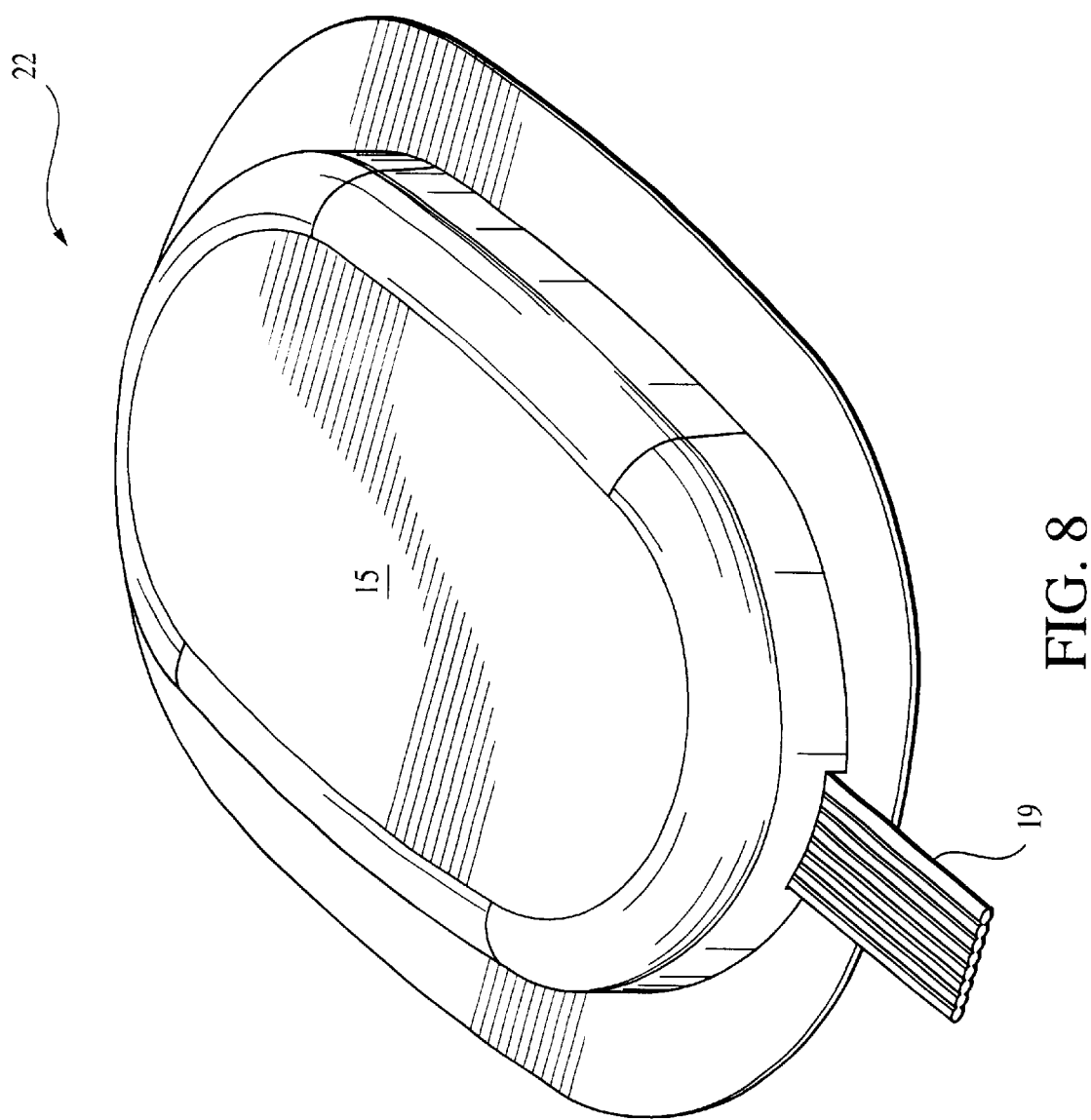
FIG. 8 is an enlarged perspective view of a CPR pad.
Figure 8A:
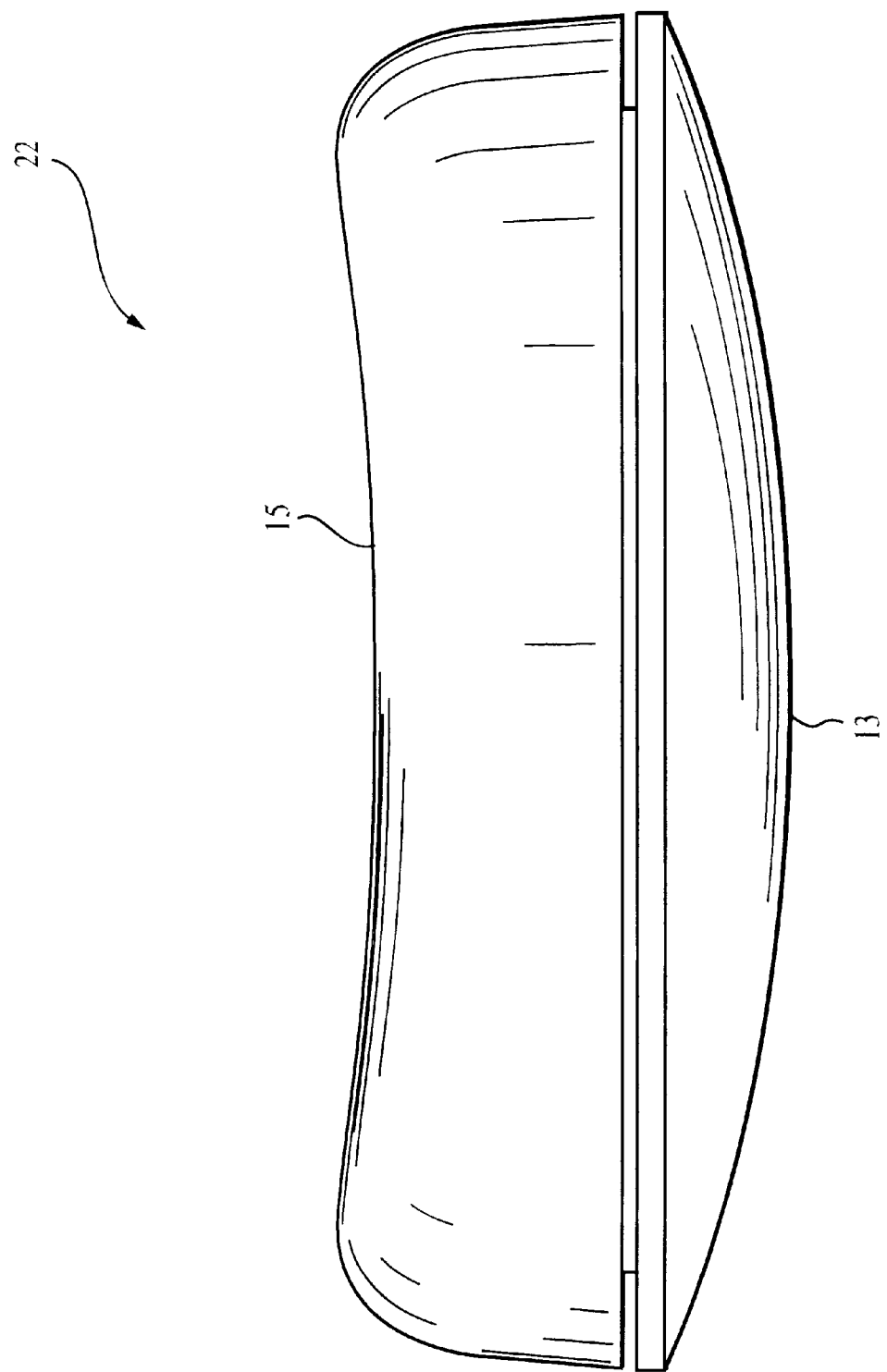
FIGS. 8A and 8B are, respectively, a side view and side cross-sectional view of the pad.
Figure 8B:
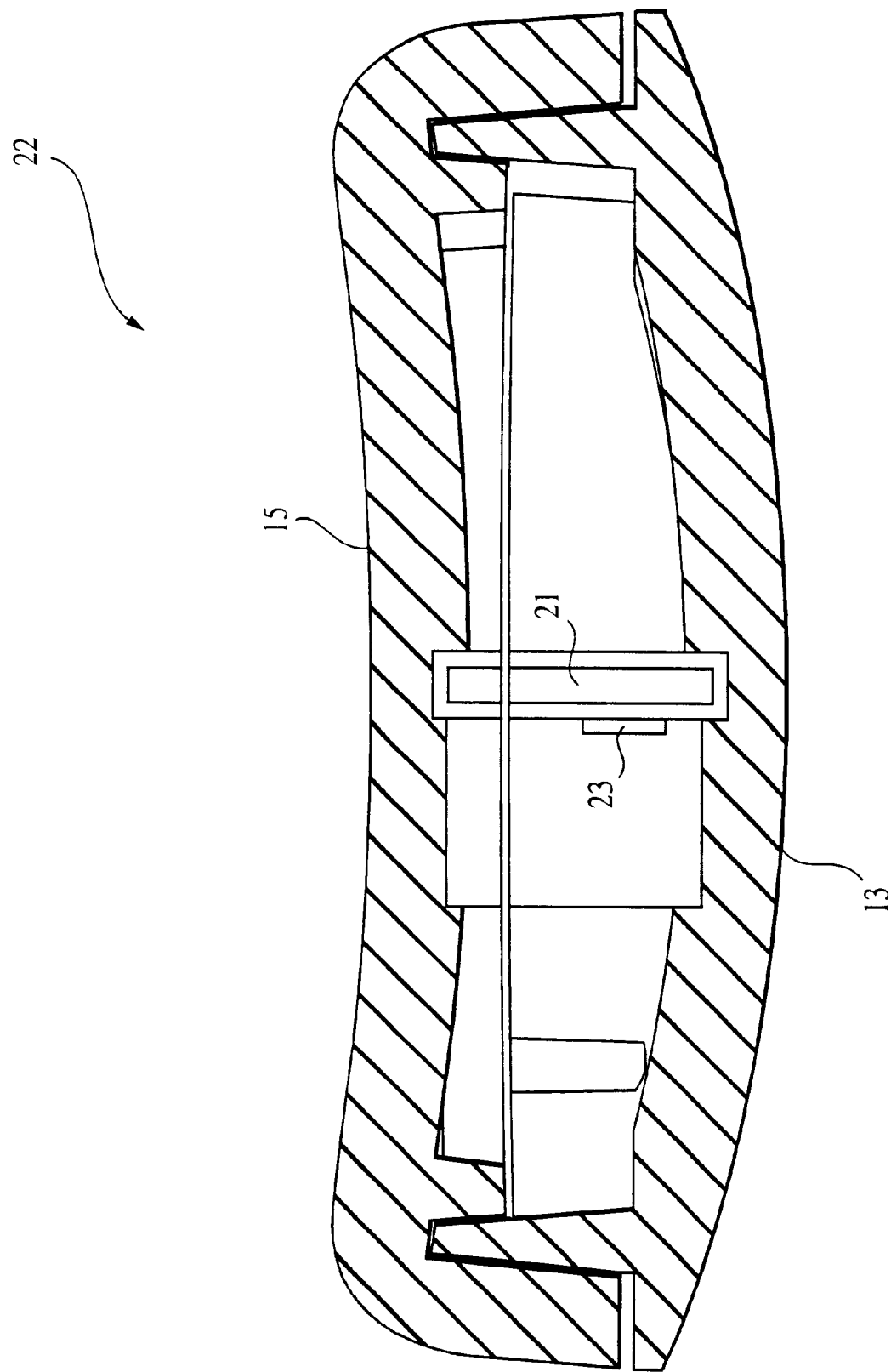

The CPR pad is shown in more detail in FIGS. 8–8B. As shown, it is preferred that the CPR pad 22 have a convex bottom surface 13, to conform to the patient's sternal notch area, and a concave top surface 15, to facilitate hand placement when CPR compressions are delivered through the CPR pad. The CPR pad 22 may include electronics, enclosed within the pad, to monitor the depth and rate of CPR compressions. For example, as shown in FIG. 8B, an accelerometer 21 and circuit board 23 may be positioned inside the CPR pad 22 and connected to the control box of the defibrillator, e.g., by a cable 19 (FIG. 8). The control box includes electronics, e.g., a microprocessor, that analyze the data acquired by the accelerometer and generate audio and/or visual prompts to advise the caregiver of the sufficiency or insufficiency of CPR compression rate and depth. For example, an audio prompt can be provided to advise the caregiver that more force should be applied during chest compressions.

Foldable Structure

Figure 2:
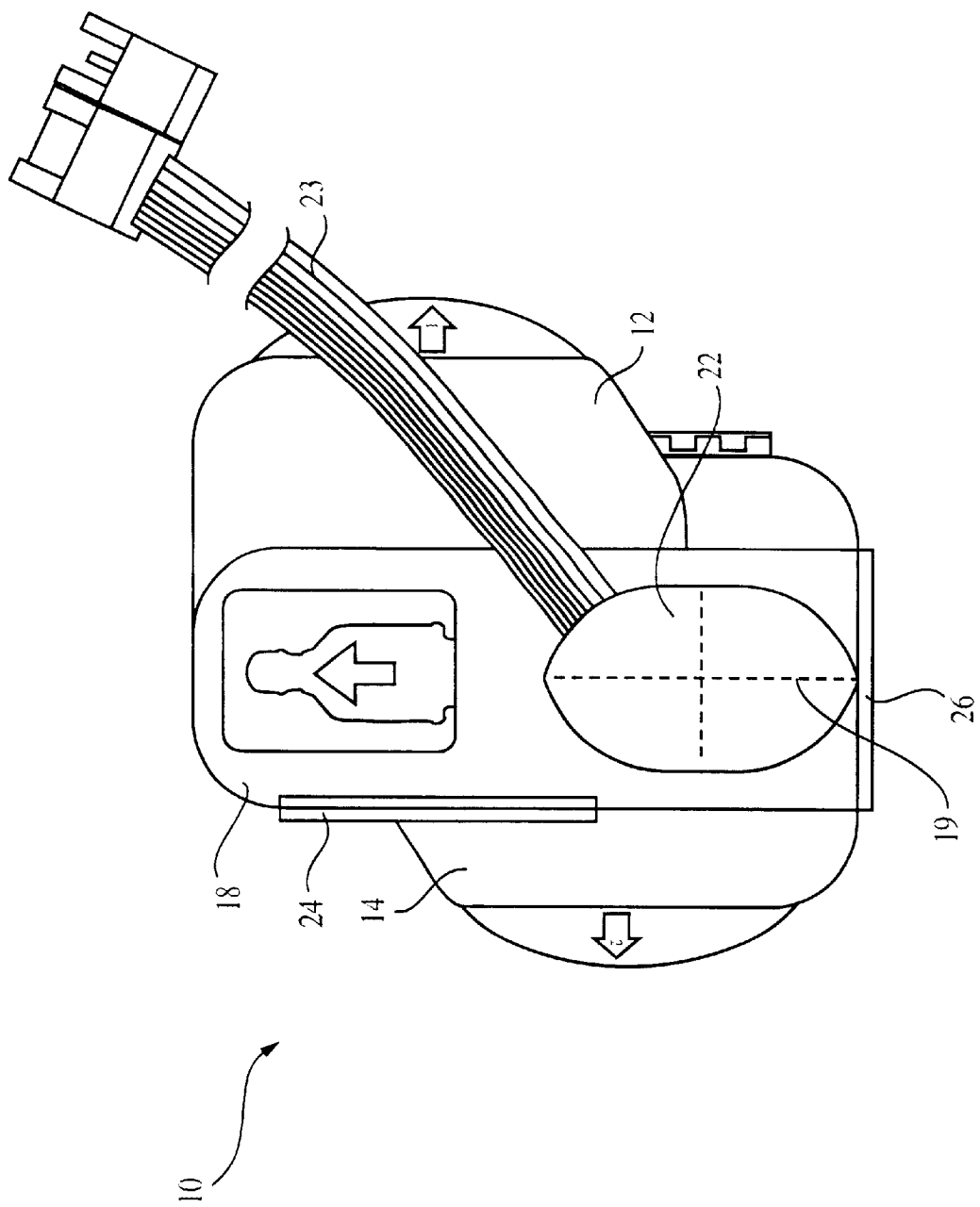
FIG. 2 is a top view of the electrode assembly of FIG. 1 in its folded state.

The flexible webs 24, 26 and the separable hinge 28 allow the electrode assembly to be folded, as shown in FIG. 2. Folding the electrode assembly allows it to be easily and conveniently stored, e.g., inside the case of a defibrillator. The separable hinge also allows the apex electrode 14 to be extended for proper positioning on large individuals, as will be discussed below with reference to FIG. 3.

Preferably, webs 24 and 26 are each at least about 1 cm wide, to allow enough slack for the components of the electrode assembly to be easily folded. The flexible webs may be formed of any desired tear-resistant flexible sheet material, e.g., fabric, elastomeric sheet materials, plastic sheet materials, or composite sheet materials such as TYVEK sheet material.

As shown in FIG. 2, the electrode assembly is preferably folded so that the CPR pad 22 is on top. This configuration generally results in the most compact size, and also allows the caregiver to grasp the CPR pad 22 and unfold the electrode assembly simply by gently shaking it and allowing the electrodes to open out.

Electrode Assembly Shape

The shape of the electrode assembly facilitates quick and accurate placement by both lay and skilled caregivers when the puck is correctly positioned. The sternum and apex electrodes extend substantially perpendicular to the central member 16. The electrodes are spaced along the length of the central member so that when the sternum electrode 12 is correctly positioned on the patient's upper chest, a diagonal line drawn between the sternum electrode and apex electrode will pass through the ventricular area of the heart for patients having relatively normal chest sizes. (Patients having unusually large chest sizes are accommodated by extension of the apex electrode, as will be discussed below.)

Figure 5:
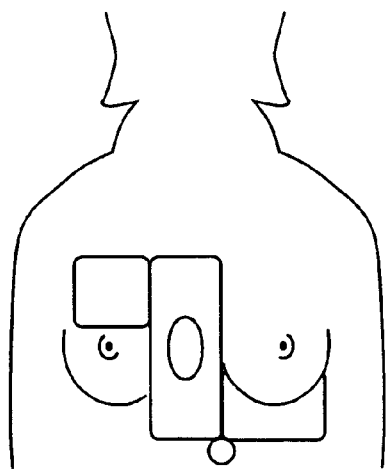
FIG. 5 is a diagrammatic view of the electrode assembly of FIG. 1 positioned on a female patient.

This "stairstep-like" shape of the electrode assembly avoids difficulties with placement that are presented by body contours such as breast tissue and chest lumps. For example, as shown in FIG. 5, if a patient has large breasts, the apex electrode can simply be positioned under the breast tissue, without disturbing the positioning of the rest of the electrode assembly.

The flexible connections between the components of the electrode assembly also facilitate placement around body contours. For example, when the electrode assembly is applied to a barrel-chested individual, the flexible connection between the electrodes and the central member allows the electrode assembly to conform to the curvature of the patient's body.

Preferably, the upper central portion 18 is relatively narrow, so that it will fit in the valley between closely spaced breasts. It is preferred that width W of upper central portion 18 is less than about 9 cm, typically from about 6 to 9 cm. The lower center portion 20 may be wider, since it is below the breast area during use, and generally needs to be wider to accommodate the internal lead wires. The width of lower center portion is typically about 7 to 11 cm. Electrode size is dictated in part by the minimum active area requirements of medical device standards such as AAMI DF-2 and DF-39. As a result of these requirements, the area of each electrode is typically about 75 $cm^2$, (50 $cm^2$ minimum per electrode, and a minimum total area for both electrodes of 150 $cm^2$).

Applying the Electrode Assembly to a Patient

Figure 4:
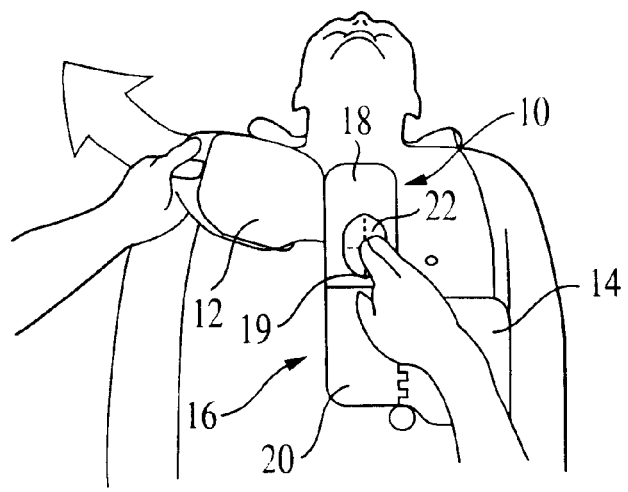
FIGS. 4 and 4A are diagrammatic perspective views showing the electrode assembly of FIG. 1 being placed on a patient by a caregiver.
Figure 4A:
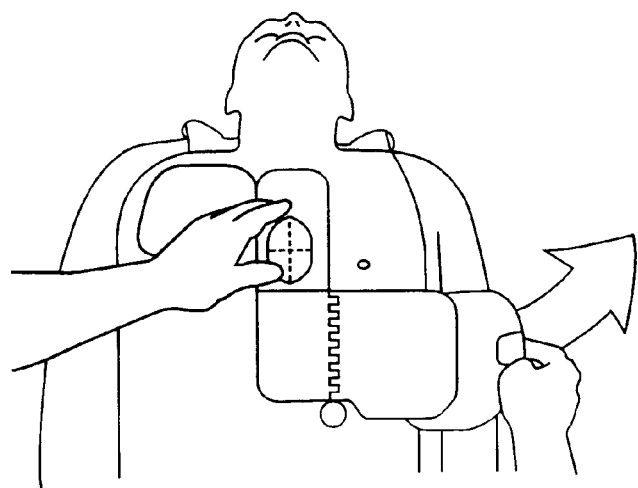
Figure 7:
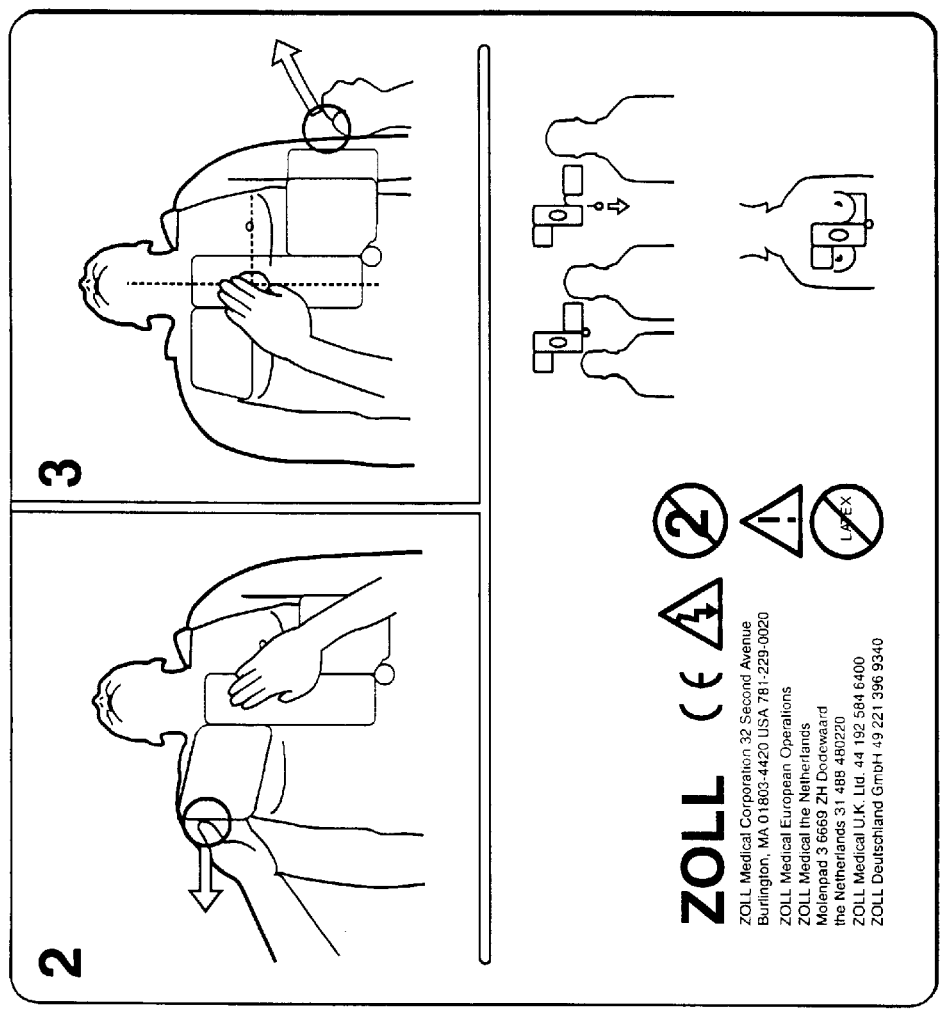
FIG. 7 is an example of a label indicating the proper sequence of steps for applying the electrode assembly of FIG. 1.

The electrode assembly is applied to a patient as shown in FIGS. 4 and 4A. As discussed above, the caregiver first unfolds the electrode assembly, e.g., by grasping the CPR pad 22 and allowing the electrodes to open out. Next, using the cross-hairs 19, the caregiver aligns the electrode assembly 10, as discussed above, by aligning the horizontal cross-hair with the patient's nipples and the vertical cross-hair with the center of the patient's sternum. Labeling printed on the electrode assembly or provided on the packaging (e.g., as shown in FIG. 7) provides the caregiver with visual instructions on where to place the electrode assembly on the patient. Numbers are used to show the recommended sequence of steps the caregiver should follow in applying the electrode. After the electrode is properly aligned, the caregiver presses down lightly on the CPR pad 22 while pulling the pull tab 40 of the release paper protecting the sternum electrode (FIG. 4). The caregiver then gently presses the sternum electrode into contact with the patient's skin, and repeats this process with the apex electrode (FIG. 4A). At this point, the electrode assembly is ready for use.

Figure 4B:
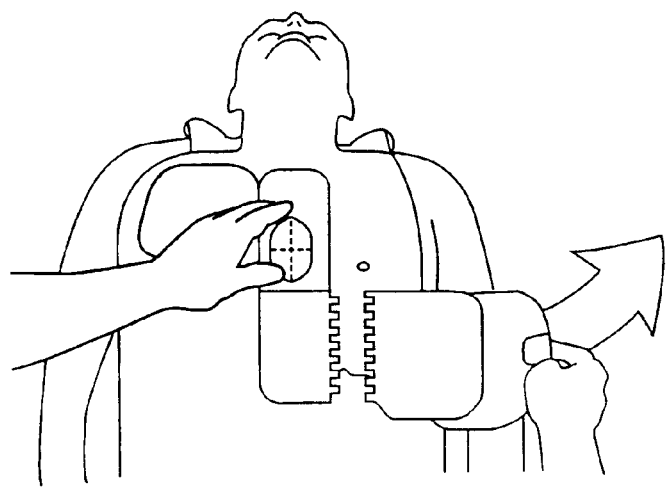
FIG. 4B is a diagrammatic perspective view showing the electrode assembly in position on a patient with the apex electrode separated and extended.

As shown in FIG. 4B, if the patient is a very large person, or has a large chest or girth, it may be necessary to extend the apex electrode as discussed above and shown in FIG. 3. The caregiver can determine whether this is necessary by examining whether a diagonal line drawn between the center of the sternum electrode and center of the apex electrode would be likely to pass through or near the victim's heart. If not, then the apex electrode should be extended by pulling locking pin 30 out and drawing extra lead wire 32 out of the lower central portion 20. The extended apex electrode is then adhered to the patient in the manner discussed above.

Electrode Assembly Materials

The body of the electrode assembly may be formed of any desired material. Foam sheet materials, for example a closed cell polyethylene foam, will provide resiliency and compliance to the skin surface of the patient.

The electrodes may be any type of electrode suitable for use in defibrillation, and generally include a conductor, such as tin; an electrolyte, such as a hydrogel; and lead wires to connect the conductor to a cable. Suitable electrodes for defibrillation are well known in the medical electrode field. The electrodes may include corrosion inhibiting features, e.g., as described in U.S. Pat. No. 6,019,877, the disclosure of which is incorporated herein by reference.

The separable hinge may be formed of any rigid or semi-rigid material, and is preferably formed of an electrically non-conductive material for enhanced safety. Moldable plastics facilitate manufacture of the hinge. An example of a suitable moldable plastic is polycarbonate.

Suitable materials for webs 24 and 26 are discussed above in the Foldable Structure section.

The CPR pad may be formed of any material that is sufficiently rigid to support the caregiver's hand during chest compressions. Preferably the CPR pad is formed of an electrically non-conductive material for enhanced safety. Suitable materials include plastics and elastomers.

Release Sheets

Figure 6:
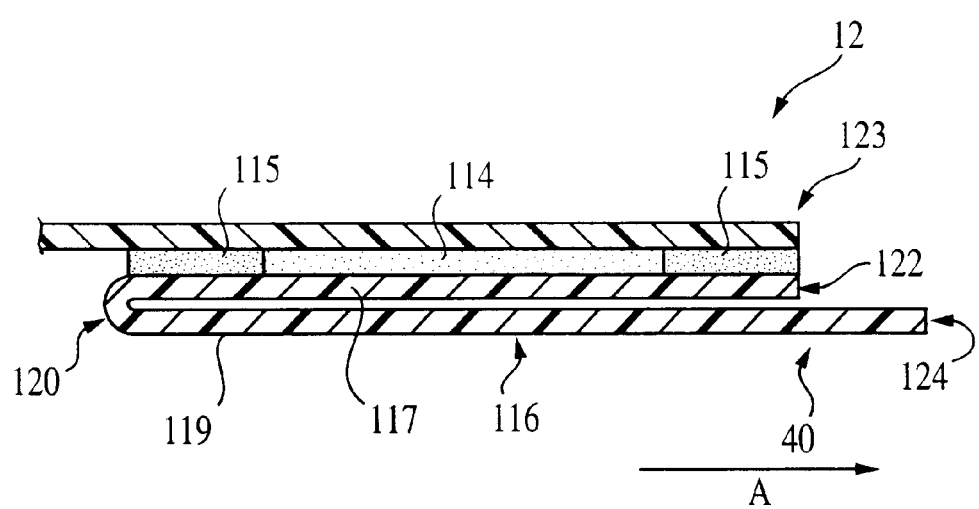
FIG. 6 is a cross-sectional view of an electrode pad according to one embodiment of the invention.
Figure 6A:
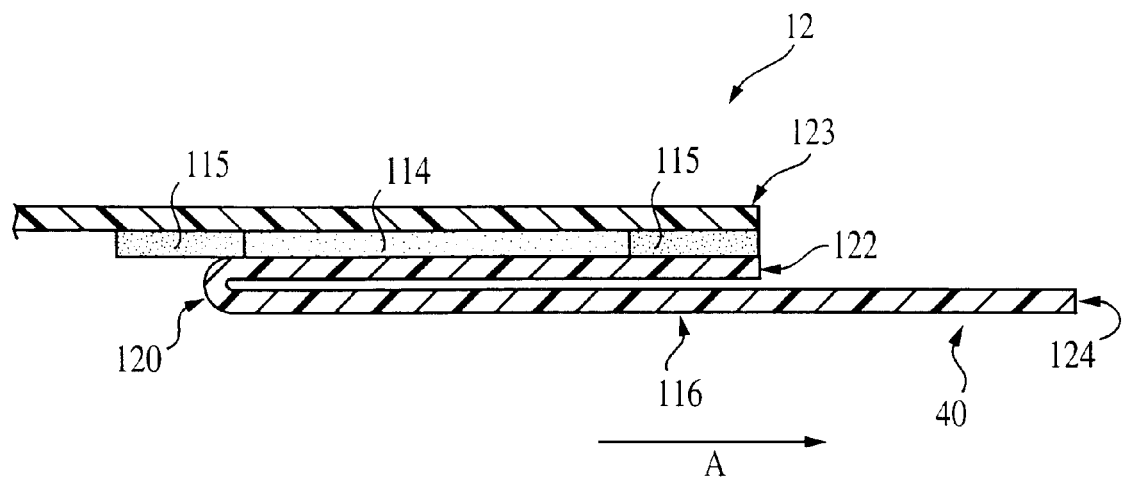
FIGS. 6A and 6B are similar cross-sectional views, illustrating removal of the release sheet.
Figure 6B:
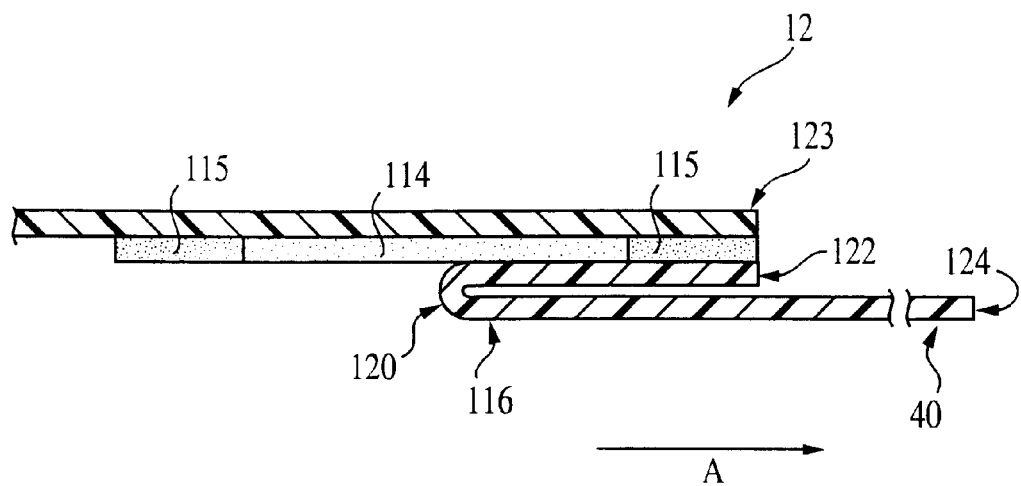

A preferred release sheet construction is shown in FIGS. 6–6B. Referring to FIG. 6, electrode 12 includes, a conductive gel layer 114, an adhesive ring 115, and a release sheet 116.

Release sheet 116 is folded, at fold 120, to define a generally U-shaped configuration, defining a portion 117 that is initially adhered to the adhesive and gel, and a portion 119 that extends freely beyond fold 120. The release sheet is folded in a manner so that it will not unfold to any significant extent during storage or prior to use. The release sheet may also be held in place, e.g., by a pair of tabs (not shown) extending from portion 117, under which pull tab 40, discussed below, is disposed prior to use, or by a small area of pressure sensitive adhesive positioned in the same general area, on portion 117 or portion 119, to adhere the two portions together until use.

The end 122 of the release sheet that is adjacent the gel layer 114 is generally substantially aligned with the edge 123 of the electrode pad. The opposite end 124 of the release sheet extends beyond the edge 123 of the electrode pad, providing a pull-tab 40 which can be grasped by a user. Pull tab 40 preferably extends far enough beyond the edge 123 to provide a good grasp between the thumb and forefinger, typically at least about 1 inch.

To apply electrode 12 to a patient, a caregiver positions the electrode on the patient's chest in a desired position. When the caregiver is sure that the electrode is in the correct position, the caregiver holds the electrode in place, grasps pull tab 40, and peels the release sheet 116 out from underneath the electrode as indicated by arrow A in FIG. 6.

As the release sheet 116 is peeled off (FIGS. 6A and 6B), the fold 120 moves across the electrode pad in the direction of arrow A, so that the gel layer 114 is exposed and brought into contact with the patient's skin. As the gel layer and adhesive are exposed, the electrode adheres to the patient's skin and electrical contact is established. Light pressure may be applied to the electrode by the caregiver to ensure good adhesion.

The release sheet may be a release-coated paper, a plastic sheet material (including non-polymeric films having the properties of plastics), a polymeric film, or any other suitable sheet material having release properties sufficient to release from the gel layer and adhesive. Suitable sheet materials for use in the embodiment described above are also foldable. Examples of suitable sheet materials include polystyrene, polyester and paper.

Other Embodiments

Other embodiments are within the scope of the following claims.

Importantly, each of the features discussed above, i.e., the foldable structure, the CPR pad, the positioning cross-hairs, the shape of the electrode, and the separable hinge, can be used individually or in any desired combination. For example, a foldable electrode assembly may be provided with none of the other features, or with only those features that are desired.

Moreover, instead of a separable hinge, as shown, the apex electrode may be separably joined to the central member in any desired manner, including strips of hook and loop fastener material (such as VELCRO fastener material) or other cooperative fastening strips such as strips coated with pressure sensitive adhesive. The electrode may also be separably joined by a tear-away arrangement, e.g., a perforated area between the electrode and central member.

As noted above, the CPR pad may be omitted. If the CPR pad is omitted, the cross-hairs may be printed or embossed directly on the surface of the central member 16 (e.g., on upper central portion 18 in the embodiment described above), or may also be omitted if desired.

Although generally it is only the positioning of the apex electrode that needs to be adjusted to accommodate large individuals, as discussed above, a separable hinge may be provided between the sternum electrode and the upper central portion 18 if desired.

Although it is generally preferred that the central member have foldable portions, as discussed above, for optimal foldability, the central member may be a single piece that is not foldable, or is not hinged, if desired. Similarly, as noted above, all of the foldable features may be omitted and the electrode assembly may be a non-foldable part that includes one or more of the other features discussed above.

While it is preferred that the release sheet be removable while the electrode is positioned against the patient's skin, as discussed above, any desired type of release sheet configuration may be used, including release sheets that are removed prior to placing the electrode against the patient's skin.

Moreover, while cross-hairs formed of two perpendicular dotted lines have been shown in the embodiment discussed above, other configurations may be used if desired to provide the positioning features described above.

What is claimed is:

1. An electrode assembly for use with a defibrillator, comprising
   a pair of electrodes configured to be attached to a patient's chest, to acquire data indicative of the patient's heart rhythm and to deliver a defibrillating shock if appropriate; and a central member joining the electrodes and configured to be attached to the patient's chest; the electrodes being folded about the central member during storage prior to attachment to the patient's chest.

2. The electrode assembly of claim 1 wherein the electrodes are folded along defined hinge regions.

3. The electrode assembly of claim 1 wherein the electrodes are positioned about the central member to facilitate their placement on the chest in an optimal position for the delivery of defibrillation therapy.

4. The electrode assembly of claim 1 wherein at least one of the electrodes is joined to the central member by a web of flexible material.

5. The electrode assembly of claim 4 wherein the web is at least 1 cm wide.

6. The electrode assembly of claim 1 further comprising a CPR pad, mounted on the central member.

7. The electrode assembly of claim 6 wherein the CPR pad is configured to be pressed upon by a caregiver during the delivery of CPR chest compressions.

8. The electrode assembly of claim 6 wherein the CPR pad is located on the assembly so that when it is placed on the patient's lower sternum the defibrillation electrodes are properly placed for the delivery of defibrillation therapy.

9. The electrode assembly of claim 6 wherein the CPR pad includes a sensor constructed to acquire data indicative of the depth and rate of CPR compressions.

10. The electrode assembly of claim 1 wherein at least one of said electrodes is configured to be optionally separable from the central member.

11. The electrode assembly of claim 10 wherein said separable electrode is separably joined to the central member by a separable flexible fastener.

12. The electrode assembly of claim 11 wherein said separable flexible fastener comprises a separable hinge.

13. The electrode assembly of claim 11 wherein said separable flexible fastener comprises a hook and loop fastener tape.

14. The electrode assembly of claim 1 wherein the central member includes two portions that are foldable upon each other.

15. The electrode assembly of claim 1 wherein the electrodes have a combined active area of at least 150 cm2.

16. The electrode assembly of claim 1 wherein each electrode has an active area of at least 50 cm2.

17. The electrode assembly of claim 16 wherein each electrode has an active area of at least 75 cm2.

18. The electrode assembly of claim 1 further comprising indicia on an exposed surface of the electrode assembly, the indicia including a first portion and a second portion, the indicia being positioned so that alignment of the first portion with a patient's nipples and alignment of the second portion with the patient's sternum will correctly position the electrodes on the patient's chest for effective defibrillation treatment.

19. The electrode assembly of claim 18 wherein the indicia are disposed on a CPR pad mounted on the central member.

20. The electrode assembly of claim 18 wherein the indicia are disposed on a surface of the central member.

21. The electrode assembly of claim 1 wherein the electrodes extend substantially transversely from opposite sides of the central member in a spaced relationship.

22. An electrode assembly for use with a defibrillator, comprising an apex electrode and a sternum electrode, the electrodes being configured to be attached to a patient's chest, to acquire data indicative of the patient's heart rhythm and to deliver a defibrillating shock if appropriate; and a central member joining the electrodes;

wherein one of the electrodes is configured to be optionally separated mechanically from the central member but to remain electrically connected to the defibrillator, and wherein the separably joined electrode is separably joined to the central member by a separable flexible fastener.

23. The electrode assembly of claim 22 wherein said separable flexible fastener comprises a separable hinge.

24. The electrode assembly of claim 23 wherein said separable hinge includes a locking pin constructed to be removed by a caregiver to separate the hinge.

25. The electrode assembly of claim 22, said separable flexible fastener comprises a hook and loop fastener tape.

26. The electrode assembly of claim 11 or 22 wherein the separable flexible fastener includes a tear-away strip.

27. An electrode assembly for use with a defibrillator, comprising an apex electrode and a sternum electrode, the electrodes being configured to be attached to a patient's chest, to acquire data indicative of the patient's heart rhythm and to deliver a defibrillating shock if appropriate; and a central member joining the electrodes;

wherein one of the electrodes is configured to be optionally separated mechanically from the central member but to remain electrically connected to the defibrillator, and wherein the separably joined electrode, after separation from the central member, is joined to the central member only by an electrical connector.

28. An electrode assembly for use with a defibrillator, comprising a pair of electrodes configured to be attached to a patient's chest, to acquire data indicative of the patient's heart rhythm and to deliver a defibrillating shock if appropriate;

a central member joining the electrodes; and a CPR pad positioned on the central member;

the electrodes being folded about the central member in a manner so that the CPR pad is on top and can be grasped by a caregiver to unfold the electrode assembly.

29. The electrode assembly of claim 28 wherein the electrodes are folded in a manner so that when the CPR pad is grasped by a user the electrodes fall open in the general position in which the electrodes should be applied to the patient.

30. An electrode assembly for use with a defibrillator, comprising an apex electrode and a sternum electrode, the electrodes being configured to be attached to a patient's chest, to acquire data indicative of the patient's heart rhythm and to deliver a defibrillating shock if appropriate; and a central member joining the electrodes and being configured so that when the assembly is applied to the chest of the patient the central member extends generally along the centerline of the chest and has two longitudinal ends, one closer to the head and the other closer to the feet of the patient;

wherein the electrodes extend generally transversely from opposite sides of the central member in a spaced relationship, with one electrode extending toward the right side of the patient and from the longitudinal end of the central member closest to the head, and the other electrode extending toward the left side of the patient and from the longitudinal end of the central member closest to the feet.

31. The electrode assembly of claim 30 wherein the electrodes are positioned about the central member to facilitate their placement on the chest in an optimal position for the delivery of defibrillation therapy.

32. The electrode assembly of claim 30 wherein the electrodes are positioned about the central member to minimize contact of the electrodes with breast tissue of the patient.

33. The electrode assembly of claim 32 wherein the apex electrode is joined to the central member by a hinge, allowing the apex electrode to be maneuvered around breast tissue.

34. The electrode assembly of claim 30 wherein the central member is elongated.

35. The electrode assembly of claim 30 the electrodes have a combined active area of at least 150 cm2.

36. The electrode assembly of claim 30 wherein each electrode has an active area of at least 50 cm2.

37. The electrode assembly of claim 36 wherein each electrode has an active area of at least 75 cm2.

38. The electrode assembly of claim 30 wherein the electrodes and central member define a "stairstep-like" shape.

39. The electrode assembly of claim 34 wherein the central member is dimensioned to fit in the valley between the breasts of the patient.

40. The electrode assembly of claim 30 further comprising a CPR pad, mounted on the central member.

41. The electrode assembly of claim 30 wherein the electrodes are folded about member.

42. The electrode assembly of claim 41 wherein the central member includes two portions that are foldable upon each other.

43. The electrode assembly of claim 30 the electrodes extend substantially perpendicular to the central member.

* * * * *

UNITED STATES PATENT AND TRADEMARK OFFICE
CERTIFICATE OF CORRECTION

PATENT NO. : 6,782,293 B2
DATED : August 24, 2004
INVENTOR(S) : Michael R. Dupelle et al.

It is certified that error appears in the above-identified patent and that said Letters Patent is hereby corrected as shown below:

Column 10,
Line 8, delete the comma "," and insert -- wherein --.

Column 11,
Line 11, after "30", insert -- wherein --.

Column 12,
Line 9, after "about", insert -- the central --.
Line 13, after "30", insert -- wherein --.

Signed and Sealed this

Twenty-seventh Day of September, 2005

JON W. DUDAS
*Director of the United States Patent and Trademark Office*